Jan. 6, 1959 A. J. RESTANI Plant Pat. 1,794
ROSE PLANT
Filed April 14, 1958
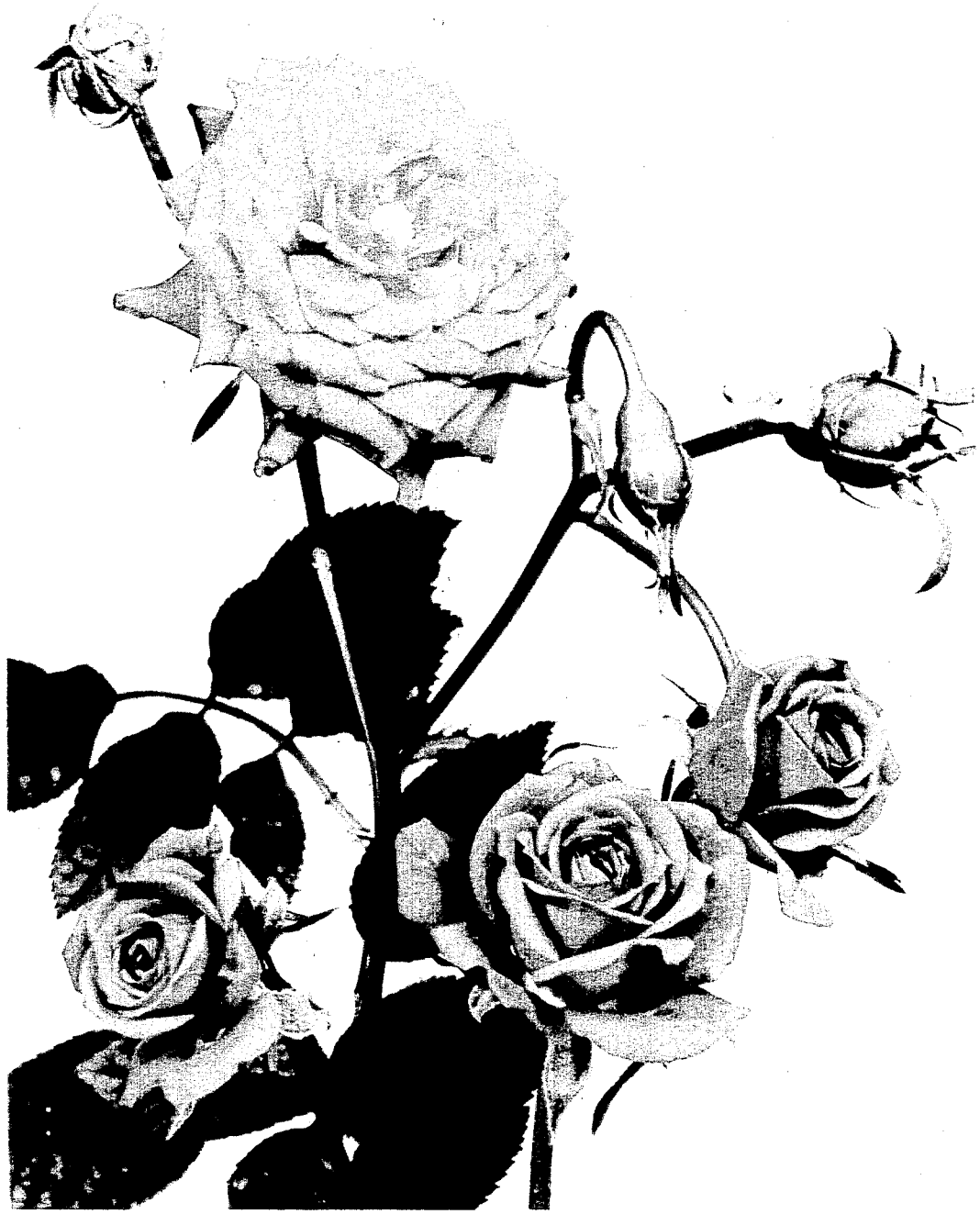
INVENTOR.
Albert J. Restani
BY
Fryer & Johnson
Attorneys United States Patent Office Plant Pat. 1,794
Patented Jan. 6, 1959

1,794

ROSE PLANT

Albert J. Restani, San Francisco, Calif.

Application April 14, 1958, Serial No. 728,502

1 Claim. (Cl. 47—61)

This invention relates to a new rose plant variety particularly adapted for greenhouses to permit the continuous supply of blooms to florists for the full twelve months of the year. The novel characteristics of this rose include its ability to hold its true red color until the petals fall.

This new rose is a sport of a rose known as "Garnette," an unpatented hybrid polyantha or floribunda of European origin being originated by Mathais Tantau of Uetersen, Holstein, Germany from a cross of Rosenelfe × Eva seed and introduced into the United States in 1947 and commonly grown in greenhouses and furnishing blooms used by florists throughout the United States. Both the new rose and its parent rose have extreme usefulness in that they permit the continuous supply of blooms to florists for the full twelve months of the year.

An important feature of this sport of "Garnette" is its truer red color and its ability to hold its true red color without fading or bluing until the petals fall. The more numerous (60–78) petals of the new rose against the (25–30) petals of its parent gives it a better form both in bud and open flower. The new rose has other good features such as a longer lasting quality as a cut flower, the plant is more floriferous, the leaves are much larger and the overall growth habit of the plant is a great improvement upon the parent plant.

The new rose has been asexually reproduced and its distinctive characteristics have come true to form in the reproductions.

The accompanying illustration shows seven blooms of the new rose, including a bud, a partially opened flower and a fully opened flower.

The following is a detailed description of the new rose; and the colors designated were taken from the Horticulture Color Chart II of the British Color Council.

*General information*

Type: Tall bush plant particularly adapted for greenhouse growing to supply flowers for the cut flower trade.

Class: Hybrid polyantha.

Sport: Of an unpatented rose known as "Garnette," and it was discovered on October 7, 1955 while cutting bloom of "Garnette" stock.

Propagation: By cutting, grafting and layering conducted at San Francisco, California. The variety has retained its distinguishing characteristics through succeeding propagations.

*Flower*

Locality where grown: San Francisco, California.

Flowers borne: Several to the stem in clusters and on strong, long stems.

Quantity of bloom: Abundant under greenhouse conditions.

Continuity: Continuous.

Fragrance: Slight spicy.

Bud: Medium peduncle. Bud is medium, erect, light green with few green prickles.

Before calyx breaks, bud is medium, globular, with foliaceous appendages on the surface of the bud, and with slender much cut foliaceous parts extending beyond the tip of the bud equal to three-quarters or more of its length.

As calyx breaks, the color is Tyrian Rose #24.

As first petal opens its size is medium and its form is ovoid; the outside color is Tyrian Rose #24 and the inside color is Rose Red #724. It opens up well.

Bloom: The size when fully open is medium and is one and three-fourths to two and one-fourth inches.

Petalage is double with from sixty to seventy-eight petals arranged regularly, usually with no stamens showing. The form has a high center at first, becoming flat and globular, with the petals remaining at first tightly rolled outward, and becoming later, at maturity, very tightly rolled outward.

Petals: Thick, leathery, with inside velvety and outside shiny.

*Shape.*—Outside petals are obovate, with one notch, and intermediate petals are obovate with one notch. Inside petals are also obovate with one notch.

*Color.*—The colors in a newly opened flower grown in a greenhouse in October, 1957 at San Francisco, California are as follows: Outside, intermediate and inner petals—outside surface: Tyrian Rose #24; inside surface—Rose Red #724.

The colors in a rose open for three days grown in a greenhouse at San Francisco, California in October, 1957 are as follows: Outside, intermediate and inner petals—outside surface: Shiny Tyrian Rose #24; inside surface—Velvety Rose Red #724.

The general color effect is Velvety Rose Red #724 in the newly opened flower, with the color Velvety Rose Red #724/3 after the flower is open three days.

Behavior: Petals drop off cleanly.

Flower longevity: Cut flowers kept at living room temperature six to seven days in October.

*Reproductive organs*

Stamens: Many, arranged irregularly, mixed with petaloids.

Filaments: Yellow with anthers.

Anthers: Small, yellow, open at various times.

Pollen: Abundant, yellow.

Pistils: Many.

Styles: Uneven, and bunched.

Stigma: Light yellow.

Ovaries: All enclosed in calyx.

Hips: Globular, or pear-shaped, prickly, with yellow and russet color.

Sepals: Spear-shaped.

*Plant*

Foliage:

*Leaves.*—Compound of five or seven with many leaflets, and leaves very abundant, large, moderately soft and heavy.

*Leaflets.*—Oval, lanceolate, with apex acute, base round and margin serrated.

*Color.*—In mature plant the upper surface is dark green and the under surface is light green. In young foliage, the upper surface is green, and orange; and the under surface is light green and bronze.

*Rachis.*—Heavy. Upper side—hairy. Under side—thorny.

*Stipules.*—With short points turning out at an angle of less than 45°, recurved toward the stem.

Growth:

*Habit.*—Upright, much branched.

*Growth.*—Free and vigorous.

*Canes.*—Heavy.

*Main stems.*—Green. Thorns—few, long, straight extending downward with long narrow base. Prickles—few, green. Hairs—none.

*Branches.* — Green, bronze. Thorns — none. Prickles—few, green. Hairs—none.

*New shoots.*—Green or red. Thorns—very few, straight with long, narrow base. Prickles—few, reddish. Hairs—none.

Having thus described my rose plant I claim:

A new and distinct variety of rose plant of the polyantha class, substantially as herein shown and described, retaining the free habit of bloom that enables its parent variety to supply blooms continuously during all seasons under greenhouse conditions, and characterized particularly as to novelty by its true red color that is held without fading until the petals fall, the large number of petals that number about two times as many as those of its parent, the better form of the rose as a bud and as an open flower, and the longer lasting nature of cut flowers obtained from the rose plant.

No references cited.